(12) United States Patent
Gerlach et al.

(10) Patent No.: US 6,932,242 B2
(45) Date of Patent: Aug. 23, 2005

(54) SYRINGE PUMP

(75) Inventors: Hans-Joseph Gerlach, Marsberg (DE); Martin Sippel, Melsungen (DE)

(73) Assignee: B. Braun Melsungen AG, Melsungen (DE)

( * ) Notice: Subject to any disclaimer, the term of this patent is extended or adjusted under 35 U.S.C. 154(b) by 230 days.

(21) Appl. No.: 10/601,210

(22) Filed: Jun. 20, 2003

(65) Prior Publication Data

US 2004/0057855 A1 Mar. 25, 2004

(30) Foreign Application Priority Data

Jun. 20, 2002 (DE) ..................................... 202 09 581 U

(51) Int. Cl.$^7$ ............................................. A61M 37/00
(52) U.S. Cl. ...................... 222/113; 222/156; 222/182; 222/327; 222/333; 222/386; 604/131; 604/155
(58) Field of Search .............................. 222/113, 154, 222/156, 182, 327, 333, 386; 604/131, 155

(56) References Cited

U.S. PATENT DOCUMENTS

| | | | | |
|---|---|---|---|---|
| 4,424,720 A | * | 1/1984 | Bucchianeri | ................ 222/390 |
| 4,437,859 A | * | 3/1984 | Whitehouse et al. | ........ 604/131 |
| 4,529,401 A | * | 7/1985 | Leslie et al. | ................. 604/131 |
| 4,652,260 A | * | 3/1987 | Fenton, Jr. et al. | ......... 604/154 |
| 4,858,607 A | * | 8/1989 | Jordan et al. | ................ 606/182 |
| 5,295,967 A | * | 3/1994 | Rondelet et al. | ............ 604/154 |
| 5,505,709 A | * | 4/1996 | Funderburk et al. | ........ 604/155 |
| 5,545,140 A | * | 8/1996 | Conero et al. | .............. 604/154 |
| 5,891,104 A | * | 4/1999 | Shonfeld et al. | ............ 604/195 |
| 5,954,697 A | * | 9/1999 | Srisathapat et al. | ......... 604/155 |
| 6,019,745 A | * | 2/2000 | Gray | .......................... 604/131 |
| 6,221,045 B1 | * | 4/2001 | Duchon et al. | ............. 604/151 |
| 2003/0009133 A1 | * | 1/2003 | Ramey | ........................ 604/155 |

* cited by examiner

*Primary Examiner*—Kenneth Bomberg
(74) *Attorney, Agent, or Firm*—Osha Liang LLP; John W. Montgomery

(57) ABSTRACT

The syringe pump comprises a housing (10). The operating panel (32) is situated on a swiveling lid (30) on the front side of the housing (10). The lid (30) further comprises a window (34) with a magnifying device (35) through which the user can view the syringe. The invention allows for a miniaturization of the syringe pump in a highly densified modular system. The lid (30) may further include a lighting means for illuminating the syringe.

7 Claims, 3 Drawing Sheets

SYRINGE PUMP

RELATED APPLICATIONS

This application claims priority from German Patent Application No. 202 09 581.9, filed on Jun. 20, 2002, incorporated herein by reference for all legitimate purposes and relied upon for priority.

FIELD OF INVENTION

This invention relates to a syringe pump comprising a housing presenting a syringe trough for a syringe to be placed therein, an operating panel and a drive head for moving a plunger of the syringe, the drive head being movable linearly with respect to the housing.

BACKGROUND OF THE INVENTION

In modern intensive-care medicine large numbers of infusion apparatus find increasing use. A single intensive-care site can comprise up to twenty infusion pumps. This requires a compact design of the infusion pumps. Therefore, they should be designed small in size.

DETAILED DESCRIPTION OF THE ILLUSTRATIVE EMBODIMENTS

Figure 1:
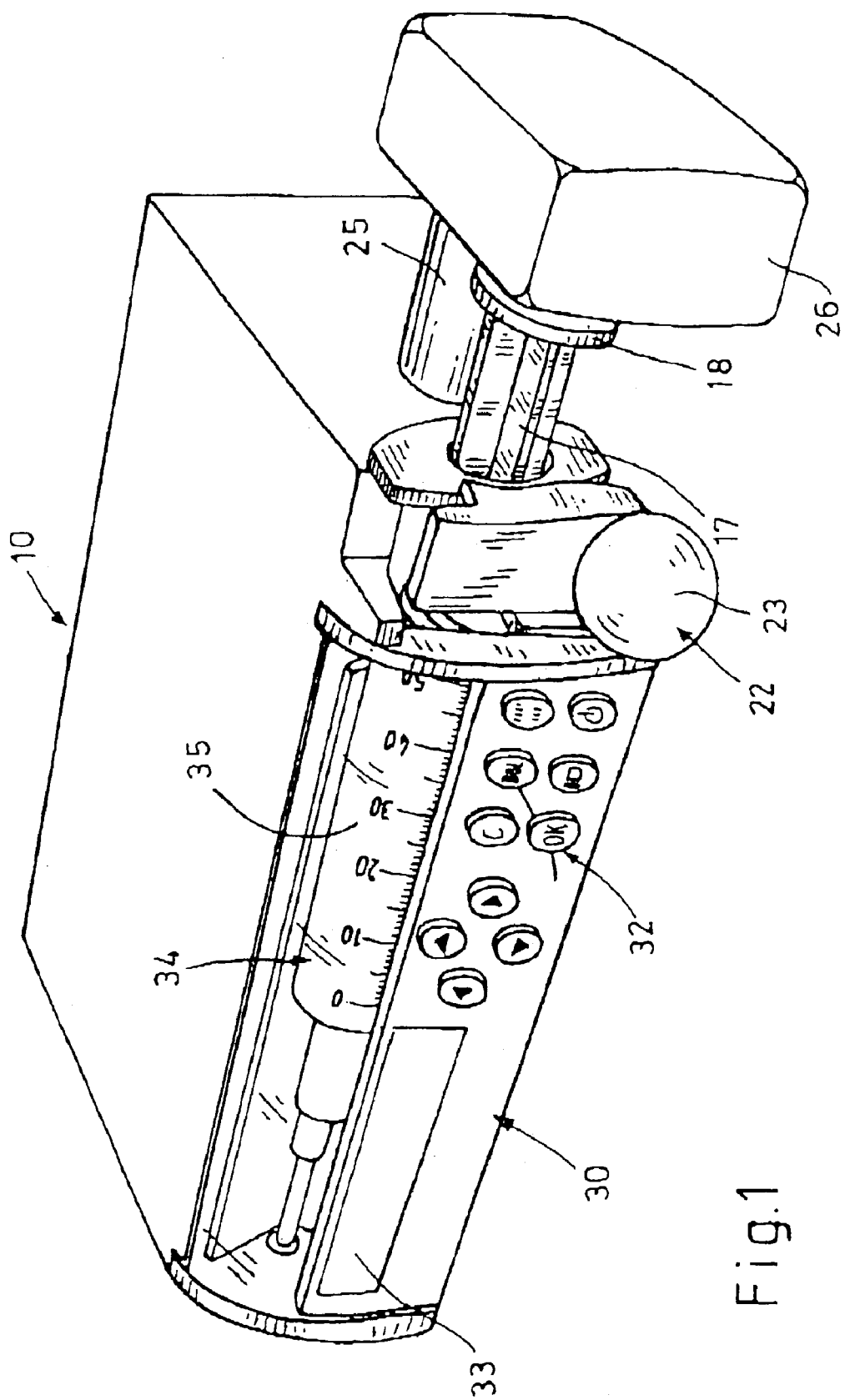
FIG. 1—is a perspective view of the syringe pump with the lid closed.
Figure 2:
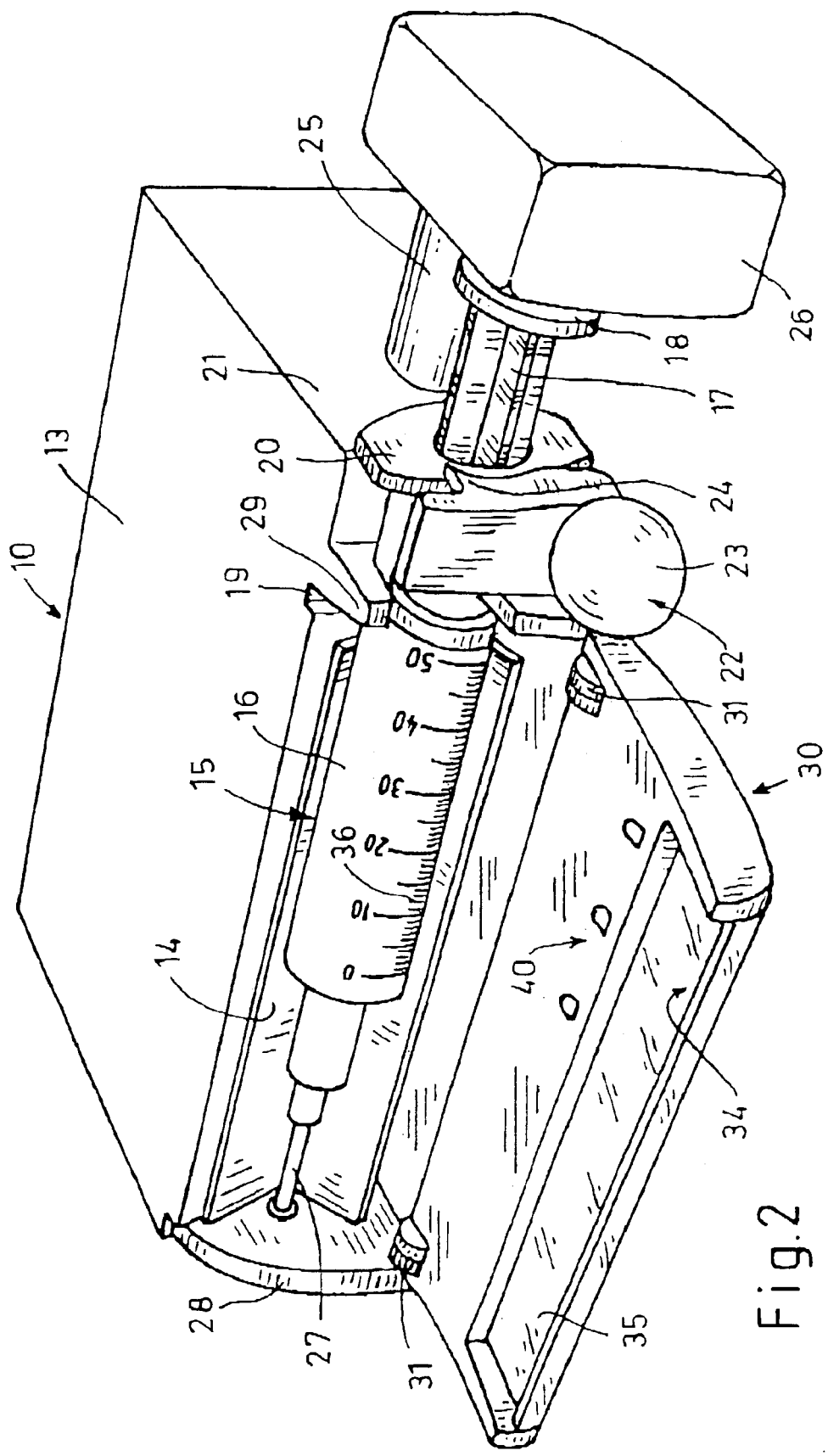
FIG. 2—illustrates the syringe pump with the lid opened.

The following is a detailed description of an embodiment of the invention with reference to the drawings. FIGS. 1 and 2 show a syringe pump comprising a housing 10 in the form of a flat box. At the front side of the housing 10, a horizontal syringe trough 14 is located, into which a syringe 15 may be placed. The syringe 15 has a syringe barrel 16 and a plunger therein, connected to a plunger rod 17. A piston plate 18 is arranged at the end of the plunger rod 17. The proximal end of the syringe barrel 16 is provided with a syringe lug 20 set against a syringe bearing 21 of the housing to secure the syringe against axial displacement.

The housing 10 is further provided with a syringe bracket 22 adapted to be manually pulled out to the front and having a handle 23 for that purpose. The syringe bracket 22 is drawn towards the syringe 15 by a spring, whereby the bracket 22 pushes the syringe against the syringe trough 14. The position of the syringe bracket 22 is detected and electronically evaluated to thereby determine the syringe size. The syringe bracket 22 has a blade 24 partially extending over the syringe lug 20, which may engage the plunger rod 17 to act as a piston brake. The blade 24 can be moved in a controlled manner.

To move the syringe piston relative to the syringe barrel 16, the housing 10 is provided with a drive rod 25 that can be extended from a front end face of the housing and has a drive head 26 at its end. The drive head 26 includes a gripping device that grips and holds the piston plate 18. By a controlled movement of the drive rod 25, the plunger rod 17 is advanced to expel the contents of the syringe 15. An infusion line 27 leading to a patient is connected to the distal end of the syringe 15.

The syringe trough 14 extends along a front side of the housing 10 between one end wall 28 and an intermediate wall 29 of the housing. The syringe trough 14 is closed with a lid 14 hinged to a lower front edge of the housing by hinges 31. In the closed state, the lid 30 abuts on the end wall 28, the intermediate wall 29 and a top wall 13 of the housing.

As illustrated in FIG. 1, the front face of the lid 30 includes an operating panel 32 comprising various keys for operation by the user. Further, a front face of the lid comprises a display device 33. The operating panel 32 and the display device 33 are electrically connected to a processor within the housing.

The operating panel 32 and the display device 33 extend over only a part of the height of the lid 30. The upper part of the lid 30 is provided with a transparent window 34. The window 34 contains a cylinder lens forming a magnifying device 35. With the lid 30 closed, the magnifying device 35 magnifies the syringe and especially a scale 36 on the syringe. The focal length of the magnifying device is greater than the distance a between an object and the magnifying device for the smallest syringe usable.

Figure 3:
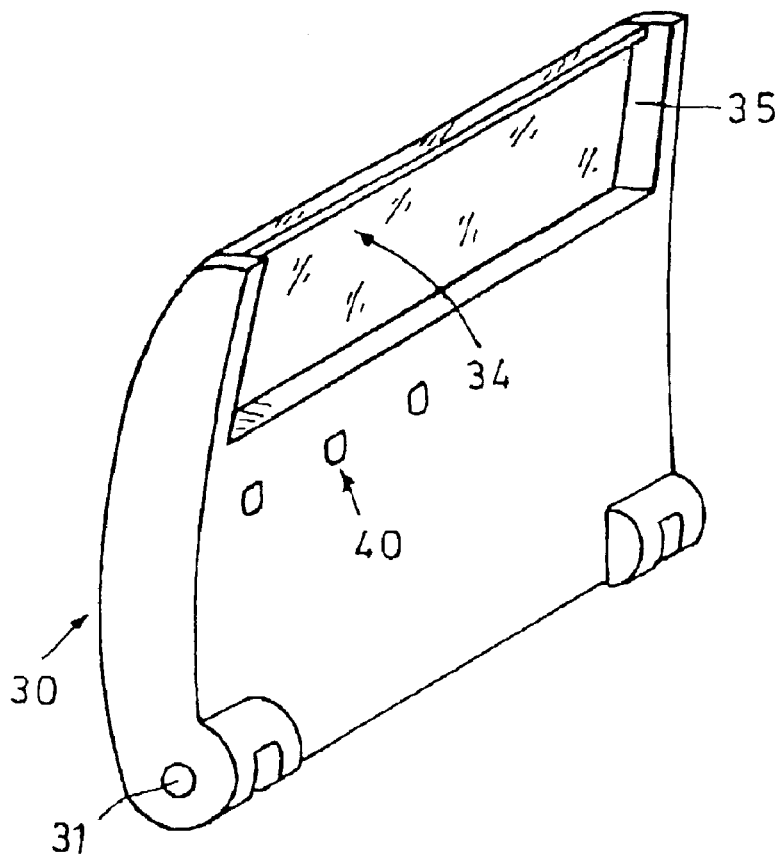
FIG. 3—is a perspective view of the lid.

FIGS. 2 and 3 show the lid 30 including a lighting device 40 which in the present embodiment has three light sources emitting light towards the syringe 15. The lighting device may serve, on the one hand, to illuminate the syringe, but, in case of a syringe alarm, may also serve as a signaling means to identify the syringe pump causing the alarm.

A part of the lid is designed as a magnifying means so as to provide the user a magnified representation of the relevant portion of the syringe. Such an optical magnification is especially useful if the syringe pump is suitable for syringes of different formats. With small syringes, the scale and the numbers are necessarily small in size. In this case, the magnifying means brings the surface of the syringe lying deep down in the syringe trough to the eye of the viewer in a magnified form. Thereby, it is avoided that the user first has to visually search for a small syringe and then has to undergo the trouble of reading a minuscule scale. Even if the viewer is further away and the viewing angle is unfavorable, a small syringe can be read easily.

Figure 4:
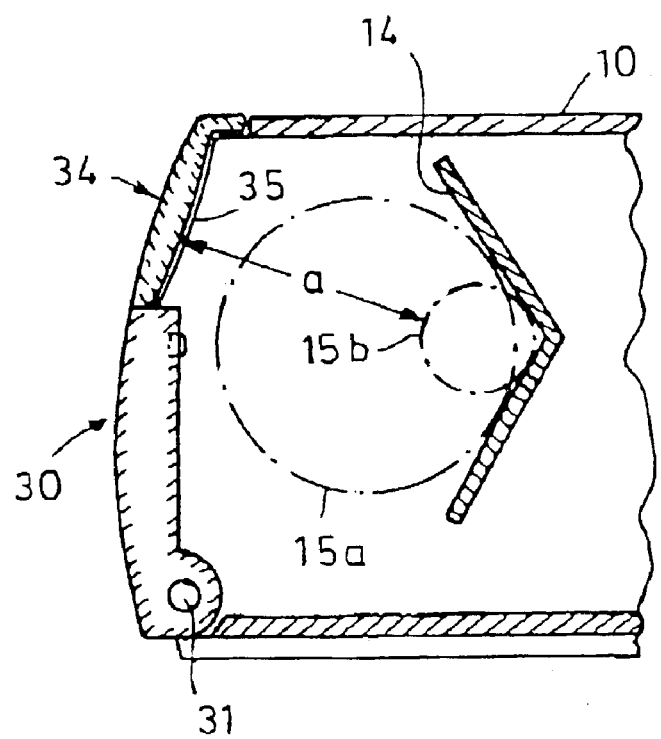
FIG. 4—is a sectional view for illustrating the suitability of the syringe pump for different syringe sizes.

FIG. 4 illustrates that syringes of different sizes can be placed into the syringe trough 14, being orientated such that they can be viewed through the magnifying device 35. A circumference of a large syringe, is defined by an imaginary line at 15a, whereas the circumference of a small syringe is defined by an imaginary line at 15b.

According to one embodiment of the invention, a swiveling lid covering at least a part of the syringe trough comprises a magnifying means for a magnified representation of the syringe surface, which optically magnifies the syringe surface of syringes of different sizes whose diameters differ by at least the factor 2.

The invention provides a syringe pump which, despite its small size, allows for a good readability of the syringes inserted therein.

VARIATIONS AND EQUIVALENTS

It is understood that variations may be made in the foregoing without departing from the scope of the invention. For example, the magnifying device is disclosed in one embodiment as a cylinder lens and could also be another type of magnifying lens or device for optical magnification without departing from certain aspects of the invention.

Also, while the lighting device 40 has been described as included in the lid 30, alternate constructions with the lighting device 40 included in the trough 14 to illuminate the syringe 15 may also be used without departing from certain aspects of the invention. The lid can include a lighting conducting light into the syringe trough. As an alternative, the lighting device can be provided at the syringe trough. The assistance provided by a lighting device is particularly useful in darkened environments. Moreover, lighting can also draw attention to special conditions of an apparatus, e.g. to indicate an alarm. To this end, special light colors may also be activated.

Spatial references such as "bottom", "top", "front", "back", "lower", "upper", "under", and "central" are for purposes of illustration only, relative to the figures shown and are not limited to the specific orientation of the structure or movement directions as described.

Although only a few exemplary embodiments of this invention have been described in detail above, those skilled in the art will readily appreciate that many other modifications are possible in the exemplary embodiments without materially departing from the novel teachings and advantages of this invention. Accordingly, all such modifications are intended to be included within the scope of this invention as defined in the following claims.

What is claimed is:

1. A syringe pump comprising:

a housing (10) with a syringe trough (14) for a syringe (15) to be placed therein;

a drive head (26) for moving the syringe plunger of the syringe, the drive head being movable linearly with respect to the housing (10);

an operating panel (32) connected to the housing; and a swiveling lid (30) covering at least a part of the syringe trough (14), the swiveling lid (30) comprising a magnifying device (35) for a magnified representation of the syringe surface, the magnifying device (35) capable of optically magnifying the syringe surface of syringes (15a, 15b) of different sizes whose diameters differ by at least the factor 2.

2. The syringe pump of claim 1, wherein the magnifying device (35) comprises an elongate cylinder lens.

3. The syringe pump of claim 2, wherein the lid (30) comprises a lighting device (40) for illuminating the syringe (15) in the syringe trough (14).

4. The syringe pump of claim 2, wherein the syringe trough (14) comprises a lighting device (40) for illuminating the syringe (15) in the syringe trough (14).

5. The syringe pump of claim 1, wherein the lid (30) comprises a lighting device (40) for illuminating the syringe (15) in the syringe trough (14).

6. The syringe pump of claim 1, wherein the syringe trough (14) comprises a lighting device (40) for illuminating the syringe (15) in the syringe trough (14).

7. The syringe pump of claims 1, 2, 3, 4, 5 or 6, wherein the lid (30) includes the operating panel (32) and a display device (33).

* * * * *